(12) United States Patent
Lezdey et al.

(10) Patent No.: US 6,174,859 B1
(45) Date of Patent: Jan. 16, 2001

(54) METHOD OF TREATMENT

(75) Inventors: John Lezdey, Voorhees, NJ (US);
Darren Lezdey, Indian Rock Beach, FL (US)

(73) Assignee: J & D Sciences, Inc., Safety Harbor, FL (US)

(*) Notice: Under 35 U.S.C. 154(b), the term of this patent shall be extended for 0 days.

(21) Appl. No.: 09/286,740

(22) Filed: Apr. 6, 1999

(51) Int. Cl.[7] ................................................ A61K 38/00
(52) U.S. Cl. .................................. 514/12; 514/912
(58) Field of Search .................................................. 514/12

(56) References Cited

U.S. PATENT DOCUMENTS 5,604,201 * 2/1997 Thomas et al. ........................ 514/12

* cited by examiner

Primary Examiner—Zohreh Fay
(74) Attorney, Agent, or Firm—John Lezdey & Assoc

(57) ABSTRACT

The present invention provides a method and composition for treating eye and ear infections from parasites and eye and ear infections, characterized by the presence of pseudomonas and increased kallikrein and kinin activity. The compositions contain a protease inhibitor selected from the group consisting of alpha 1-antitrypsin, secretory leucocyte protease inhibitor and antiplasmin inhibitor, a steroidal antiphlogistic compound, and a non-steroidal antiphlogistic compound and optionally hyaluronic acid.

19 Claims, No Drawings

METHOD OF TREATMENT

FIELD OF THE INVENTION

The present invention relates to a method of treating eye and ear infections resulting from parasites and/or infections characterized by the presence of pseudomonas, increased kallikrein and kinin activity. More particularly, there is provided compositions containing a protease inhibitor selected from the group consisting of alpha 1-antitrypsin (AAT), secretory leucocyte protease inhibitor (SLPI) and anti-plasmin inhibitor.

BACKGROUND OF THE INVENTION

Arachidic acid is liberated in damaged, wounded, or inflamed tissues from phospholipids of cytoplasmatic membranes by the action of phospholipase enzyme and may be then metabolized by the cyclooxygenase cycle (by lipoxygenase enzyme) to prostanoids and eicosanoids. Antiphlogistics of both the steroid and nonsteroid nature, antibiotics, and sulfonamides are often used for therapeutic purposes. The antibiotics which specifically suppress pathogenic microbes and are often used in ophthalmology, are tetracycline, chloramphenicol, bacitracin, and neomycin. Therapeutics which prevent the development of inflammation (antiphlogistics) are both steroid and nonsteroid. The steroid antiphlogistics (e.g., dexamethasone block phospholipase. The anti-inflammatory drugs of nonsteroid nature (e.g., indomethacin, flurbiprofen, pirprofen) block cyclooxygenase and others. The blockage of these enzymes is important, because the products formed in metabolic cycles have a strong chemotactic effect (they cause accumulation of leukocytes in the sites of origin), (e.g., some leucotrienes) and increase the vascular permeability. This contributes to an excess development of the inflammation. Inflammations, (both of infectious and noninfectious origin) are very dangerous for the anterior and posterior segments of the eye. Thus, scars formed in the cornea during the final stage of the healing process cause the loss of an exceptional function of this tissue, i.e. transparency. The loss of transparency of optical media of the eye (cornea, lens) then leads to a reduction or even loss of sight.

A disadvantage of locally applied antiphlogistics is the relatively low efficiency, retarded healing, and contribution to the development of infection. The local effect of antibiotics is limited.

One of the very prospective possibilities of treatment is the inhibition of plasmin and other destruction proteases (e.g., collagenase or elastase) with specific inhibitors. These enzymes either directly develop the destruction processes (e.g., plasmin) or enable these processes by their own activity (e.g., collagenase, elastase). However, plasmin is effective not only as an initiator developing the degeneration processes proceeding in cascades, but also contributes to an excessive development of inflammation by several other mechanisms of which at least chemotaxis should be mentioned. U.S. Pat. Nos. 5,217,951; 5,290,762, and 5,190,917 which are herein incorporated by reference disclose the treatment of inflammation with serine protease inhibitors alone or in combination with a corticosteroid. None of the references teach or suggest eye and ear infections caused by parasites or relating to pseudomonas infection.

What is needed then is a medicamentous form for external use as an ophthalmologic or otolaryngologic drug.

This medicamentous form must have strong antiexudative, antiphlogistic, and antimicrobial effect. This medicamentous form is presenting lacking in the prior art.

SUMMARY OF THE INVENTION

The medicamentous form or composition of the present invention is delivered in an aqueous or ointment base particularly suited for ophthalmologic and otolaryngologic application. This medicamentous form contains inhibitors of proteases such as alpha1-antitrypsin, secretory leucocyte protease inhibitor, and anti-plasmin inhibitor trypsin and elastin. These can also be delivered with antiphlogistics and antibiotics.

Accordingly, an object of the present invention is to provide a medicamentous form having strong antiexudative, antiphlogistic and antimicrobial effects.

Still another object of the present invention is to provide a medicamentous form having therapeutic effects including the inhibition of plasmin, leucolytic elastase, and other serine proteases.

Another object of the present invention is to provide a medicamentous form that inhibits the activation of latent forms of some endoproteases and several further subsequent reactions of chemotaxis and vascularization of the cornea.

Yet another object of the present invention is to treat ear and eye infections characterized by the presence of pseudomonas, excess Kallikerin and Kinin activity.

DETAILED DESCRIPTION OF THE PREFERRED EMBODIMENT

The composition of the present invention is a medicamentous form or composition in an aqueous or ointment base particularly suitable for ophthalmologic and otolaryngologic application. The medicamentous form contains inhibitors of proteases such as alpha1-antitrypsin, secretory protease inhibitor and anti-plasmin inhibitor having a concentration of substantially 0.1 to 20 mg. per 1 ml of solution or per 1 g. of ointment base. These inhibitors are applied either individually or in combination after being dissolved in physiological saline or buffer solution with a pH of 6.5 to 7.5, which is advantageously ionically balanced (e.g., phosphate or borax buffer) or present in the ointment base.

The ionically balanced buffer solution means that sodium chloride is added to the buffer solution in such a way that the resulting solution is ionically balanced. For example, the precise performance for borax buffer with pH 7.4 is as follows:

Solution A—1.9 g. $Na_2P_4O_7$ per 100 ml $H_2O$ pro injection.

Solution B—1.25 g. $H_3BO_3$+) 0.3 g. NaCl per 100 ml $H_2$) pro injection. Anti-plasmin inhibitor provides a mix of—10 ml of solution A+90 ml of solution B.

The medicamentous form according to the preferred embodiment in the liquid state may further advantageously contain 0.05 to 15 percent by weight of thickeners selected from the group comprising hydroxypropylmethyl cellulose, methyl cellulose, polyvinylpyrrolidone, polyvinyl alcohol, poly (alkaline glycols), poly/-hydroxyalkyl, (meth)acrylates or poly(meth)acrylamides.

High concentrations of alpha1-antitrypsin or another inhibitor, when locally applied, act not only curably in the advanced stage of disease but also prospectively by the prevention of the formation of destructive processes if timely administered. The vehicles or thickeners with protracted effect then enable a longer contact of the remedy (e.g. AAT) with the tissues. The medicamentous form according to the preferred embodiment may contain 0.05 to 1.5 percent by weight of steroidal antiphlogistics such as indomethacin or 0.2 to 1 percent by weight of antibiotics such as bacitracin, meomycin, tetracycline, or chloramphenicol and/ or hyaluronic acid. Preferred is an antibiotic which is anti-pseudomonas.

The combination of protease inhibitors with antiphlogistics or antibiotics, or all substances together, increases the antiinflammatory and anti-microbial effect because the inhibitors block some products of microbes such as elastase or other proteases. This enables ont to use the antibiotics only locally and in smaller doses. The concentration of antiphlogistics may be reduced and, at the same time, the therapeutic effect is higher and the time of treatment shorter which is of great value in healing of tissue.

Ear infections are generally characterized by the presence of pseudomonas and increased tissue kallikrein and kinin activity. The more serious the infection, the greater the levels of pseudomoas, kallikrein activity and elastase. The reduction of kallikrein and kinin activity also results in reduction of pain.

Parasitic infestation of the eyes and ears has resulted in increased kallikrein activity and proteases which are released by the parasites. The common parasites which invade the eyes and ears usually through contaminated water generally express serine proteases. The protozoan parasite Cryptosporidium parvum, for example, expresses a protease-like component which is recognized by alpha 1-antitrypsin.

Shistosomiasis infections are easily started by Shistosoma mansoni entering the eyes and ears of swimmers.

Hyaluronic acid promotes healing and is especially advantageous in treating injury to the cornea.

The medicamentous form is most often applied by instillation or as an ointment into the conjunctival sac. However, it can also be used for irrigation or lubrication of the eye, facial sinuses, and external auditory meatus. It may also be injected into the anterior eye chamber and other places. The medicamentous form in the liquid state may be also present in a hydrophilic three-dimensional polymer matrix in the form of a strip, contact lens, and the like from which the active components are released. The incorporation of medicamentous form into a hydrophilic matrix can be performed according to the invention by conditioning of the matrix in the solution of medicamentous form in order to obtain the required concentration of inhibitors and also for the antiphlogistics and antibiotics in polymer matrix.

The invention is illustrated in the examples of performance and the examples are provided without the intention of limiting the scope of the present invention.

The preparation of medicamentous form in liquid state is begun by separately dissolving each substance in a small amount (10 to 40 ml) of buffer or physiological saline.

The ointment base is prepared by melting 10 g. lanolin, 10 g. liquid paraffin, and 80 g. white vaseline in bath water. The mixture is then strained through a hydrophilic gauze and sterilized. If the applicable therapeutic is easily soluble in water, it is dissolved in the necessary amount of distilled water for the preparation of injections, mixed with the ointment base in part melted in a water bath and stirred until completely cooled. If the therapeutic is insoluble in water, it is used for the preparation in the finest powdered form. However, it is first titrated in a smaller amount of liquid paraffin and then mixed with the ointment base.

EXAMPLE 1

A mixture is provided by combining alpha 1-antitrypsin hydroxypropyl methyl cellulose 1 g.; and ionically balanced borax buffer of pH 7.4 up to 100 g. Drops of this composition dosed into the conjunctival sac of a patient at intervals of 3 hours heals allergic conjunctivitis within 3 to 5 days.

EXAMPLE 2

A mixture is provided by combining alpha 1-antitrypsin 0.005 g.; hydroxypropyl methyl cellulose 2.5 g.; and ionically balanced phosphate buffer of pH 7.4 up to 100 g. The drops were dosed into the ear of a patient with swimmer's ear three times a day. Pain was reduced with the initial dose.

EXAMPLE 3

A mixture is prepared by combining alpha 1-antitrypsin 0.005 g.; polyvinylalcohol a g.; 0.001 g of hyaluronic acid and ionically balanced borax buffer of pH 7.4 up to 100 g. Drops of the mixture were applied into the conjunctival sac of the patient at intervals of 2 hours. This heals minute wounds of the conjunctive, cornea, and eyelids within 2 to 4 days.

EXAMPLE 4

A mixture is prepared by combining 0.2 g.; hydroxypropyl methyl cellulose 2.5 g.; and physiological saline up to 100 g. An etched and burnt cornea can be healed during 4 days by application of the drops four times a day. The transparency of the cornea can be recovered either completely or at least in the periphery of the cornea.

EXAMPLE 5

A mixture is prepared combining SLPI 0.01 g.; dexamethasone sodium phosphate 0.1 g.; hydroxypropyl methyl cellulose 2.5 g.; and ionically balanced borax buffer up to 100 g. The eye drops can be used to heal severe allergic conjunctivitis by instillation three times a day.

EXAMPLE 6

A mixture is prepared by combining alpha 1-antitrypsin 0.1 g.; dexamethasone sodium phosphate 0.5 g.; hydroxypropyl methyl cellulose 2 g.; 0.58 hyaluronic acid and ionically balanced phosphate buffer up to 100 g. The drops can be administered into an infected ear 3 times a day. Pain and inflammation will be reduced immediately.

EXAMPLE 7

A mixture is prepared by combining 0.1 g. of alpha 1-antitrypsin 0.05 g. of hyduronic acid 0.05 g.; dexamethasone sodium phosphate 0.1 g.; chloramphenicol 0.5 g. and physiological saline up to 100 g. The solution can be used in the treatment of rhinal allergoses and allergoses of meatus acusticus externus.

EXAMPLE 8

Ten patients from India suffering from parasitic infestation of the eyes resulting from exposure in the Ganges river and exhibiting red inflamed eyes were treated with a 5% solution of alpha 1-antitrypsin in saline solution. Immediately after the application of three drops to each of the eyes of the patients, the redness of the inflammation disappeared.

What is claimed is:

1. A method for treating optic and otic infections, inflammation and kalligrein activity by parasites and microbes which comprises administering to the site of the infection an effective amount of a protease inhibitor selected from the group consisting of alpha 1-antitrypsin, secretory leucocyte protease inhibitor, anti-plasmin inhibitor and a combination thereof in a suitable pharmaceutically acceptable carrier.

2. The method of claim 1 wherein said protease inhibitor is alpha 1-antitrypsin.

3. The method of claim 1 wherein said microbes comprise pseudomonas.

4. The method of claim 1 wherein said parasites are selected from the group consisting of Shistosoma mansoni and cryptosporidium parvum.

5. The method of claim 1 including a steroid.

6. The method of claim 5 wherein said steroids are selected from the group consisting of dexamethasone, betametasone and triamcinolone acetonide.

7. The method of claim 1 including an antimicrobial effective amount of an antibiotic.

8. The method of claim 7 wherein said antibiotic is anti-pseudomonasis.

9. The method of claim 1 including controlling kallikrein and kinin activity.

10. The method of claim 1 including a bradykinin antagonist.

11. The method of claim 1 including hyaluronic acid.

12. A method for treating otic infection characterized by elevated pseudomonas and kallikrein activity which comprises administering alpha 1-antitrypsin to the site of infection in a suitable pharmaceutical carrier.

13. The method of claim 12 including an antibiotic.

14. A method for treating optic and otic infestation by parasites which comprises administering an effective amount of alpha 1-antitrypsin to the site of infestation inflammation and kallikrein activity in a suitable pharmaceutical carrier.

15. The method of claim 14 including hyaluronic acid.

16. A composition for ophthalmologic or otolaryngologic application for patients suffering from parasitic infestation or infections characterized by the presence of pseudomonas and increased kallikrein and kinin activity which comprises:

A. about 0 to 20 mg. per milliliter of a protease inhibitor selected from the group consisting of alpha 1-antitrypsin, secretory leucocyte protease inhibitor and anti-plasmin inhibitor;

B. about 0 to 1.5 percent by weight of a steroidal antiphlogistic compound;

C. about 0 to 5 percent by weight of a non-steroidal antiphlogistic compound;

D. about 0 to 1.5 percent of hyaluronic acid, in an aqueous pharmaceutically acceptable base.

17. The composition of claim 16 wherein said antiphlogistic composition is anti-pseudomonas.

18. The composition of claim 16 comprising an effective amount of a steroid, and an effective amount of an antibiotic.

19. The composition of claim 18 including an effective amount of hyaluronic acid.

* * * * *

US006174859C1

(12) EX PARTE REEXAMINATION CERTIFICATE (6296th)

United States Patent
Lezdey et al.

(10) Number: US 6,174,859 C1
(45) Certificate Issued: Jul. 15, 2008

(54) METHOD OF TREATMENT

(75) Inventors: John Lezdey, Voorhees, NJ (US); Darren Lezdey, Indian Rock Beach, FL (US)

(73) Assignee: Alphamed Pharmaceuticals Corporation, Clearwater, FL (US)

Reexamination Request:
No. 90/007,215, Sep. 22, 2004

Reexamination Certificate for:
Patent No.: 6,174,859
Issued: Jan. 16, 2001
Appl. No.: 09/286,740
Filed: Apr. 6, 1999

(51) Int. Cl.
*A61K 38/55* (2006.01)
*A61K 38/57* (2006.01)

(52) U.S. Cl. .......................................... 514/12; 514/912
(58) Field of Classification Search ........................ None
See application file for complete search history.

(56) References Cited

U.S. PATENT DOCUMENTS

| | | | |
|---|---|---|---|
| 4,025,620 A | 5/1977 | Beyer et al. |
| 4,474,751 A | 10/1984 | Haslam et al. |
| 5,008,242 A | 4/1991 | Lezdey et al. |
| 5,061,729 A | 10/1991 | Kincses et al. |
| 5,093,316 A | 3/1992 | Lezdey et al. |
| 5,114,917 A | 5/1992 | Lezdey et al. |
| 5,134,119 A | 7/1992 | Lezdey et al. |
| 5,166,134 A | 11/1992 | Lezdey et al. |
| 5,166,331 A | 11/1992 | Della Valle et al. |
| 5,190,917 A | 3/1993 | Lezdey et al. |
| 5,215,965 A | 6/1993 | Lezdey et al. |
| 5,217,951 A | 6/1993 | Lezdey et al. |
| 5,290,762 A | 3/1994 | Lezdey et al. |
| 5,346,886 A | 9/1994 | Lezdey et al. |
| 5,492,889 A | 2/1996 | Lezdey et al. |
| 5,532,215 A | 7/1996 | Lezdey et al. |
| 5,631,241 A | 5/1997 | della Valle et al. |
| 5,679,665 A | 10/1997 | Bergamini et al. |
| 5,780,440 A | 7/1998 | Lezdey et al. |

FOREIGN PATENT DOCUMENTS

| | | |
|---|---|---|
| WO | WO 02/50287 AZ | 6/2002 |
| WO | WO 2004/045634 | 6/2004 |
| WO | WO 2004/052236 AZ | 6/2004 |

OTHER PUBLICATIONS

Baskin, G. B.. J. of Parasitology, 82:(4): 630–632, 1996.*
Schapira et all, Recombinant α1–antitrypsin Pittsburgh (Met 358→Arg) is a potent inhibitor, etc. J. Clin Invest., vol. 76, Dec. 1985, 635–637.
Iglewski, Medmicro Chapt. 27, Nov. 2, 2005.
Maeda et al "Bradykinin and Nitric Oxide in Infectious Diseases and Cancer", Immunopharmacology, Jun. 1996, 33(1–3), p. 222–30 U.S.
Avidano et al., "Analysis of protease activity in human otitis media," *Otolaryngology—Head and Neck Surgery*, 119(4):246–351 (Oct. 1998).
Bayer Corporation. Alphal–Proteinase Inhibitor (Human). Prolastin®. Revised Mar. 2003.
Centers for Disease Control and Prevention (CDC). "Swimmer's Ear" (Otitis Externa). Fact Sheet for Swimmers. Date unknown.
Coan et al., "Preparation and Properties of $Alpha_1$–Proteinase Inhibitor Concentrate from Human Plasma," *Vox. Sang.* 48:333–342 (1985).
Forney et al., "Anticryptosporidial potential of alpha–1–antitrypsin," *J. Eukaryot. Microbiol.* 43(5):63S (Sep.–Oct. 1996).
Forney et al., "Synergistic anticryptosporidial potential of the combination of alpha–1–antitrypsin and paromomycin," *Antimicrobial Agents Chemother.*, Sep. 1997, p. 2006–2008.
Abraham et al., "Mast cells in infection and immunity," *Infection Immun.* 65:3501–3508 (1997).
Boyce et al., "Mast cells: beyond IgE," *J. Allergy Clin. Immunol.* 111:24–32 (2003).
Galli et al., "Mast cells to the defense," *Nature Immunology* 4:1160–1162 (2003).
United States Food & Drug Administration, Electronic Orange Book (http://www.fda.gov/cder/ob/default.htm), visited Mar. 16, 2005, entries on dexamathasone, betamethasone, and triamcinolone.

* cited by examiner

*Primary Examiner*—Gary L Kunz

(57) ABSTRACT

The present invention provides a method and composition for treating eye and ear infections from parasites and eye and ear infections, characterized by the presence of pseudomonas and increased kallikrein and kinin activity. The compositions contain a protease inhibitor selected from the group consisting of alpha 1-antitrypsin, secretory leucocyte protease inhibitor and antiplasmin inhibitor, a steroidal antiphlogistic compound, and a non-steroidal antiphlogistic compound and optionally hyaluronic acid.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–19 are cancelled.

* * * * *